[12] United States Patent
Madani et al.

(10) Patent No.: US 10,592,779 B2
(45) Date of Patent: Mar. 17, 2020

(54) GENERATIVE ADVERSARIAL NETWORK MEDICAL IMAGE GENERATION FOR TRAINING OF A CLASSIFIER

(71) Applicant: International Business Machines Corporation, Armonk, NY (US)

(72) Inventors: Ali Madani, Oakland, CA (US); Mehdi Moradi, San Jose, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 137 days.

(21) Appl. No.: 15/850,007

(22) Filed: Dec. 21, 2017

(65) Prior Publication Data

US 2019/0197358 A1    Jun. 27, 2019

(51) Int. Cl.
| | |
|---|---|
| G16H 30/40 | (2018.01) |
| G16H 30/20 | (2018.01) |
| G06T 7/00 | (2017.01) |
| A61B 6/00 | (2006.01) |
| G06N 5/02 | (2006.01) |
| G06N 20/00 | (2019.01) |
| G06N 3/08 | (2006.01) |

(Continued)

(52) U.S. Cl.
CPC .......... *G06K 9/6259* (2013.01); *A61B 6/5217* (2013.01); *G06K 9/6267* (2013.01); *G06N 3/0454* (2013.01); *G06N 3/0472* (2013.01); *G06N 3/0481* (2013.01); *G06N 3/082* (2013.01); *G06N 5/022* (2013.01); *G06N 20/00* (2019.01); *G06T 7/0014* (2013.01); *G16H 30/20* (2018.01); *G16H 30/40* (2018.01); *G06T 2207/10116* (2013.01); *G06T 2207/30048* (2013.01)

(58) Field of Classification Search
None
See application file for complete search history.

(56) References Cited

U.S. PATENT DOCUMENTS

| 9,922,285 B1 | 3/2018 | Glode et al. |
| 9,971,958 B2 | 5/2018 | Liu et al. |
| 10,068,557 B1 | 9/2018 | Engel et al. |

(Continued)

OTHER PUBLICATIONS

List of IBM Patents or Patent Applications Treated as Related, Feb. 20, 2019, 2 pages.

(Continued)

*Primary Examiner* — Idowu O Osifade
(74) *Attorney, Agent, or Firm* — Stephen J. Walder, Jr.; William J. Stock

(57) ABSTRACT

Mechanisms are provided to implement a machine learning training model. The machine learning training model trains an image generator of a generative adversarial network (GAN) to generate medical images approximating actual medical images. The machine learning training model augments a set of training medical images to include one or more generated medical images generated by the image generator of the GAN. The machine learning training model trains a machine learning model based on the augmented set of training medical images to identify anomalies in medical images. The trained machine learning model is applied to new medical image inputs to classify the medical images as having an anomaly or not.

20 Claims, 7 Drawing Sheets

(51) Int. Cl.
  *G06N 3/04* (2006.01)
  *G06K 9/62* (2006.01)

(56) References Cited

U.S. PATENT DOCUMENTS

| | | | |
|---|---|---|---|
| 10,176,405 | B1 | 1/2019 | Zhou et al. |
| 10,242,665 | B1 | 3/2019 | Abeloe |
| 2017/0337682 | A1* | 11/2017 | Liao .................... G06T 7/30 |
| 2018/0075581 | A1 | 3/2018 | Shi et al. |
| 2018/0082150 | A1* | 3/2018 | Itou ................... G06K 9/6248 |
| 2018/0211164 | A1 | 7/2018 | Bazrafkan et al. |
| 2018/0336439 | A1 | 11/2018 | Kliger et al. |
| 2018/0336471 | A1 | 11/2018 | Rezagholizadeh et al. |
| 2019/0051310 | A1 | 2/2019 | Chang et al. |
| 2019/0080205 | A1 | 3/2019 | Kaufhold et al. |

OTHER PUBLICATIONS

Dehghan Marvast, Ehsan et al., "Automated Extraction of Echocardiograph Measurements from Medical Images", filed Dec. 20, 2017, U.S. Appl. No. 15/848,077.

Demner-Fushman, Dina et al., "Preparing a collection of radiology examinations for distribution and retrieval", Journal of the American Medical Informatics Association, vol. 23, No. 2, Jul. 2015, 18 pages.

Goodfellow, Ian J, et al., "Generative Adversarial Nets", Advances in Neural Information Processing Systems (NIPS 2014), Dec. 8-13, 2014, 9 pages.

Gur, Yaniv et al., "Towards an Efficient Way of Building Annotated Medical Image Collections for Big Data Studies", Large-Scale Annotation of Biomedical Data and Expert Label Synthesis (MICCAI Labels Workshop, Sep. 2017, 9 pages.

He, Kaiming et al., "Deep Residual Learning for Image Recognition", 29th IEEE Conference on Computer Vision and Pattern Recognition (CVPR2016), Jun. 26-Jul. 1, 2016, pp. 1-12. (Version attached: arXiv: 1512.03385v1 [cs.CV]—Dec. 10, 2015).

High, Rob, "The Era of Cognitive Systems: An Inside Look at IBM Watson and How it Works", IBM Corporation, Redbooks, Dec. 12, 2012, 16 pages.

Kingma, Diederik et ai., "Auto-Encoding Variational Bayes", Cornell University Library, arXiv:1312.6114, Dec. 20, 2013, pp. 1-9.

Kingma, Diederik P. et al., "Semi-supervised Learning with Deep Generative Models", Advances in Neural Information Processing Systems, Oct. 2014, 9 pages.

Madani, Ali et al., "Fast and accurate classification of echocardiograms using deep learning", NPJ Digital Medicine, Jun. 2017, 31 pages.

Oken, Martin M. et al., "Screening by Chest Radiograph and Lung Cancer Mortality: The Prostate, Lung, Colorectal, and Ovarian (PLCO) Randomized Trial", JAMA, vol. 306, No. 17, Nov. 2, 2011, pp. 1865-1873.

Radford, Alec et al., "Unsupervised Representation Learning with Deep Convolutional Generative Adversarial Networks", Cornell University, arXiv: 1511.06434v1, Nov. 19, 2015, 16 pages.

Ronneberger, Olaf et al., "U-Net: Convolutional Networks for Biomedical Image Segmentation", International Conference on Medical Image Computing and Computer-Assisted Intervention, Springer (2015), arXiv:1505.04597v1 [cs.CV], May 18, 2015, 8 pages.

Salimans, Tim et al., "Improved Techniques for Training GANs", In Advances in Neural Information Processing Systems, Jun. 2016, 10 pages.

Schlegl, Thomas et al., "Unsupervised Anomaly Detection with Generative Adversarial Networks to Guide Marker Discovery", International Conference on Information Processing in Medical Imaging (IPMI), Mar. 2017, 12 pages.

Wong, Ken C.et al., "Building Disease Detection Algorithms with Very Small Numbers of Positive Samples", In Medical Image Computing and Computer-Assisted Intervention (MICCAI), Sep. 2017, pp. 471-479.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

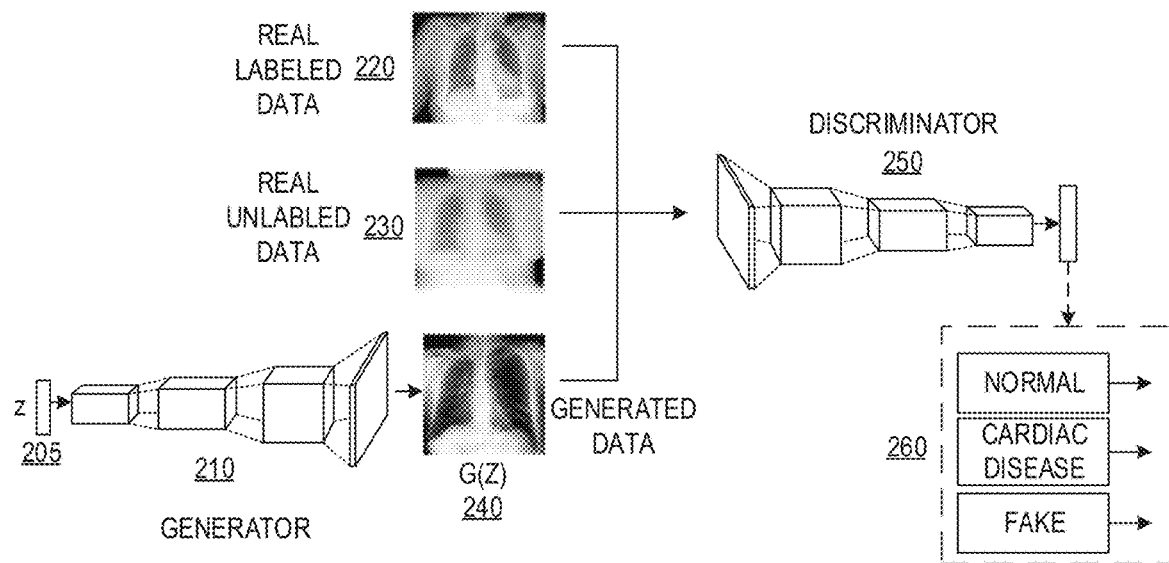
*FIG. 2B*
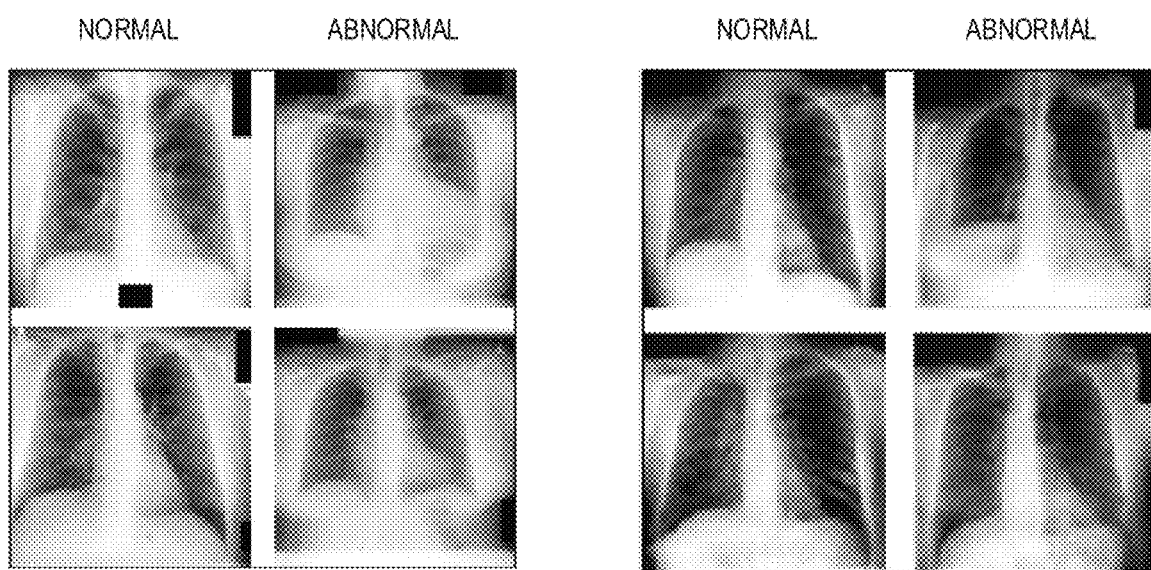
*FIG. 3*
*FIG. 4*

| LABELED DATA # | CNN ACCURACY | GAN ACCURACY |
|---|---|---|
| 10 | 51.27% | 73.08% |
| 25 | 51.27% | 75.52% |
| 100 | 57.81% | 79.58% |
| 250 | 71.23% | 81.51% |
| 500 | 78.69% | 84.25% |
| 1000 | 80.80% | 84.57% |
| 2000 | 83.12% | 85.10% |

| TRAINING SCENARIO | DATASET 2 TEST ACCURACY |
|---|---|
| CNN MODEL TRAINED ON DATASET 1 | 57.8% |
| GAN MODEL TRAINED ON DATASET 1 | 76.4% |
| SEMI-SUPERVISED GAN-BASED NET TRAINED ON LABELED DATASET 1 AND UNLABELED DATASET 2 | 93.7% |

GENERATIVE ADVERSARIAL NETWORK MEDICAL IMAGE GENERATION FOR TRAINING OF A CLASSIFIER

BACKGROUND

The present application relates generally to an improved data processing apparatus and method and more specifically to mechanisms for providing a generative adversarial network medical image generation for training a classifier.

Generative models learn a joint probability distribution p(x, y) of input variables x (the observed data values) and output variables y (determined values). Most unsupervised generative models, such as Boltzmann Machines, Deep Belief Networks, and the like, require complex samplers to train the generative model. However, the recently proposed technique of Generative Adversarial Networks (GANs) repurposes the min/max paradigm from game theory to generate images in an unsupervised manner. The GAN framework comprises a generator and a discriminator, where the generator acts as an adversary and tries to fool the discriminator by producing synthetic images based on a noise input, and the discriminator tries to differentiate synthetic images from true images.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions that are executed by the processor to configure the processor to implement a machine learning training model. The method comprises training, by the machine learning training model, an image generator of a generative adversarial network (GAN) to generate medical images approximating actual medical images. The method also comprises augmenting, by the machine learning training model, a set of training medical images to include one or more generated medical images generated by the image generator of the GAN. Moreover, the method comprises training, by the machine learning training model, a machine learning model based on the augmented set of training medical images to identify anomalies in medical images. In addition, the method comprises applying the trained machine learning model to new medical image inputs to classify the medical images as having an anomaly or not.

In some illustrative embodiments, a method is provided, in a data processing system comprising a processor and a memory, the memory comprising instructions that are executed by the processor to configure the processor to implement a generative adversarial network (GAN). The method comprises configuring a discriminator of the GAN to discriminate input medical images into a plurality of classes comprising a first class indicating a medical image representing a normal medical condition, one or more second classes indicating one or more abnormal medical conditions, and a third class indicating a generated medical image. The method further comprises generating, by a generator of the GAN, one or more generated medical images and inputting, to the discriminator of the GAN, a training medical image set comprising a first subset of labeled medical images, a second subset of unlabeled medical images, and a third subset comprising the one or more generated medical images. Moreover, the method comprises training the discriminator to classify training medical images in the training medical image set into corresponding ones of the first class, the one or more second classes, and the third class. Furthermore, the method comprises applying the trained discriminator to a new medical image to classify the new medical image into a corresponding one of the first class or one or more second classes. The new medical image is either labeled or unlabeled.

In still other illustrative embodiments, a method is provided, in a data processing system comprising a processor and a memory, the memory comprising instructions that are executed by the processor to configure the processor to implement a generative adversarial network (GAN). The method comprises training the GAN based on labeled image data, unlabeled image data, and generated image data generated by a generator of the GAN. The GAN comprises a loss function that comprises error components for each of the labeled image data, unlabeled image data, and generated image data which is used to train the GAN. The method further comprises identifying the new data source for which the trained GAN is to be adapted, and adapting the trained GAN for the new data source. Moreover, the method comprises classifying image data in the new data source by applying the adapted GAN to the data in the new data source. Adapting the trained GAN comprises obtaining a minimized set of labeled images and utilizing the minimized set of images to perform the adapting of the trained GAN.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 2A and 2B are example diagrams illustrating a semi-supervised generative adversarial network (GAN)-based architecture in accordance with one illustrative embodiment;

FIG. 3 is an example diagram illustrating example sample chest X-ray images utilized to demonstrate the advantages of the illustrative embodiments of the present invention;

FIG. 4 is an example diagram illustrating example sample generated (fake) chest X-ray images generated by a generator of the semi-supervised GAN-based architecture of the illustrative embodiments;

DETAILED DESCRIPTION

Figure 1:
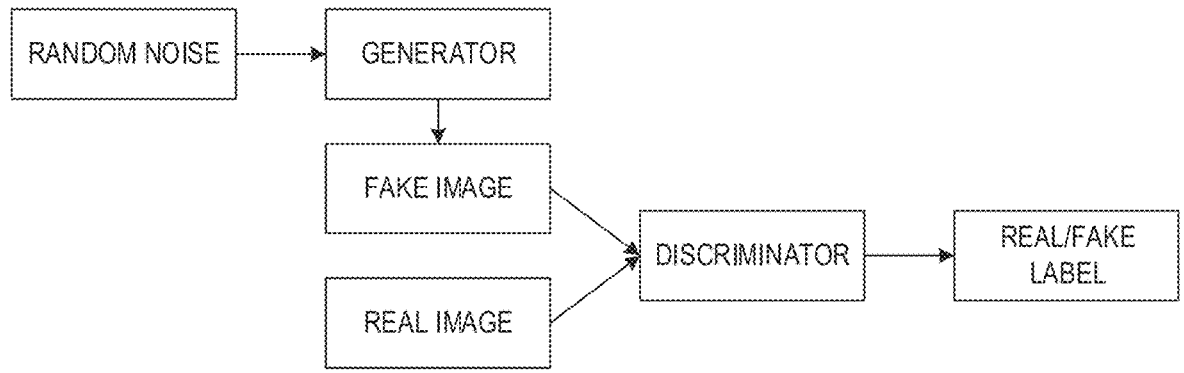
FIG. 1 is an example block diagram of a generative adversarial network (GAN)

The illustrative embodiments provide mechanisms for providing a generative adversarial network (GAN) based framework for generating medical image data and training a medical image classifier based on an expanded medical image dataset. The illustrative embodiments further provide mechanisms for selecting a training methodology, using the GAN based framework of the illustrative embodiments, to be used for new sources of medical image data, such as when a new client of a medical image classifier service begins to utilize the classifier trained by the GAN based framework. In one illustrative embodiment, the methodologies from which a training methodology is selected may comprise a first methodology in which the classifier is trained based only on a known labeled medical image source, i.e. based on labeled medical image data only, and a second methodology in which the classifier is trained based on both known labeled medical image source data and the new source's medical image data, acting as unlabeled medical image data in accordance with the illustrative embodiments.

Deep learning algorithms require large amounts of labeled (annotated) data to train effective models for the performance of cognitive operations, such as image classification or the like. In medical imaging, data is not as abundant as other computer vision fields due to privacy laws, health industry standards, the lack of integration of medical information systems, and other considerations. While efforts to alleviate these issues are ongoing, currently these efforts hamper the speed of innovation of deep learning algorithms as they inherently require large amounts of data for tasks such as image classification or semantic segmentation.

In many cases, even if medical image data is available, the data is unstructured and lacks proper labeling or annotations, e.g., labeling anatomical structures within the medical image, measurements, abnormalities, or the like. To address this, one needs to annotate the medical images. However, annotation of medical images is an expensive, time-consuming, and largely manual process. Often, one can only feasibly label (annotated) a small portion of the available unstructured medical image data while having a much larger portion of unlabeled images. As a result, medical imaging and computer vision cognitive operations are limited to being able to use only small amounts of labeled images, e.g., medical images, for use in training the classifier models, such as convolutional neural networks, of cognitive logic for performing cognitive classification operations, e.g., medical image classification tasks that identify diseases or abnormalities in the medical images.

Moreover, even if a particular labeled (annotated) image dataset is accessible for training the classifier model of the cognitive system logic, the classifier still struggles to maintain the same level of performance, e.g., accuracy, on a different medical imaging dataset from a new or never-seen data source domain. In other words, many deep learning classifiers tend to overfit to a particular data domain source. That is, for any given image classification task in medical imaging, one strives to train a classifier that separates images based on the structural or physiological variations that define the target classes. However, there are other sources of variance, such as scanner type and imaging protocol, that can differentiate images from one another. As a result, when deep learning classifiers are trained on a particular training dataset, and then tested in production on data from a different domain source, there is usually a reduction in performance.

Previously, the approach used to solve the problem of labeled (annotated) dataset scarcity, and specifically the lack of labeled medical image dataset samples in disease categories at the time of training the classifier model, was to use the available labeled dataset samples from a normal class to train a segmentation model, e.g., a neural network or other model for segmenting the medical image into separate segmented parts (sets of pixels) that are computationally easier to analyze and/or are potentially more meaningful to the classification operation. The features produced by this segmentation model are used along with the whole image to train the classifier model. This is a way of learning the distribution of data in one class, and taking advantage of the learning in distinguishing that class from other classes. This concept of "learning normal" as a way to improve abnormality classification has also been used in generative machine learning models.

Generative machine learning models have the potential to generate new dataset samples. The two main approaches of deep generative models involve either learning the underlying data distribution or learning a function to transform a sample from an existing distribution to the data distribution of interest. In deep learning, the approach of learning the underlying distribution has had considerable success with the advent of variational auto-encoders (VAEs), such as described in Kingma, et al., "Auto-Encoding Variational Bayes," arXiv preprint arXiv:1312.6114 (2013). VAEs attempt to find the variational lower bound of the probability density function with a loss function that consists of a reconstruction error and regularizer. Unfortunately, in this formulation, the bias introduced causes generated images to appear qualitatively smooth or blurry.

Generative adversarial networks (GANs) were introduced in Goodfellow, et al., "Generative Adversarial Nets," Advances in Neural Information Processing Systems, 2014. GANs utilize two neural networks referred to as a discriminator and a generator, respectively, which operate in a minimax game to find the Nash equilibrium of these two neural networks. In short, the generator seeks to create as many realistic images as possible and the discriminator seeks to distinguish between images that are real and generated (fake) images.

FIG. 1 is an example block diagram of a generative adversarial network (GAN). As shown in FIG. 1, the generator, G, takes a vector z, sampled from random Gaussian noise or conditioned with structured input, and transforms the noise to $p_G=G(z)$ to mimic the data distribution, $p_{data}$. Batches of the generated (fake) images and real images are sent to the discriminator, D, where the discriminator assigns a label 0 for real or a label 1 for fake. The cost of the discriminator, $J^{(D)}$, and generator, $J^{(G)}$, are as follows:

$$J^{(D)} = -\tfrac{1}{2} * (E_{x \sim p_{data}}[\log D(x)]) - \tfrac{1}{2} * (E_z[\log(1-D(G(z)))]) \quad (1)$$

$$J^{(G)} = -\tfrac{1}{2} * E_z[\log D(G(z))] \quad (2)$$

With an appropriate optimization technique, the neural networks of the generator G and discriminator D may be trained to reach an optimal point. The optimal generator G will produce realistic images and the optimal discriminator D will estimate the likelihood of a given image being real.

The illustrative embodiments set forth herein train a GAN for generating and discriminating medical images and utilize the generator G to create realistic medical images as a data augmentation technique for training an abnormality detector (also referred to as a classifier) that operates on medical images. For example, the medical image generation is performed by a trained generator G of the GAN while the abnormality detector, or classifier, may be implemented as the trained discriminator D of the GAN, although in some illustrative embodiments, the classifier may be a different neural network, cognitive classifier logic, or the like, which is trained based on the expanded training medical image dataset comprising a small set of labeled medical images, and a larger set of real and/or generated (fake) unlabeled medical images. In one illustrative embodiment, the medical images may be chest X-ray images, however, the present invention is not limited to such. Rather the mechanisms of the illustrative embodiments may be applied to any medical images of various anatomical portions of a biological entity, e.g., a human being, animal, or plant, using any of a variety of different medical imaging modalities, e.g., X-ray, computed tomography (CT) scan, sonogram, magnetic resonance imaging (MRI), or the like.

As noted above, medical imaging datasets are limited in size due to privacy issues and the high cost of obtaining annotations. Augmentation of a dataset is a widely used practice in deep learning to enrich the data in data-limited scenarios and to avoid overfitting. However, standard augmentation methods that produce new examples of data merely involve varying lighting, field of view, and spatial rigid transformations, for example. These modifications, while generating slightly different images, do not capture the biological variance of medical imaging data and could result in unrealistic images. In other words, the modifications made to generate new medical images for training do not improve the training because the differences are not consequential to the actual differentiation between normal and abnormal medical images evaluated by the classifier.

The illustrative embodiments recognize that generative adversarial networks (GANs) provide an avenue to understand the underlying structure of image data which can then be utilized to generate new realistic medical image samples. The illustrative embodiments utilize a GAN based mechanism for producing an augmented set of medical images, e.g., chest X-ray images in one illustrative embodiment, to increase a size of the training medical image dataset. That is, in some illustrative embodiments an architecture is provided that converts the GAN into a semi-supervised classifier for abnormality detection in medical images, trained on a fairly small size initial annotated medical image dataset. The augmented, or expanded, training medical image dataset generated by operation of the GAN of the illustrative embodiments may be used to train a convolutional neural network, or other machine learning model, or cognitive classification logic (collectively referred to as a classifier herein), to classify images with regard to abnormality presence, e.g., cardiovascular abnormalities.

In some illustrative embodiments, this classifier may be implemented as the discriminator D of the GAN, which may be implemented as a convolutional neural network. The discriminator D is trained based on labeled real medical images, unlabeled real medical images, and unlabeled generated (fake) images so as to be able to discriminate between these types of images. Thereafter, the discriminator D may be utilized with actual input medical image data to differentiate between normal and abnormal medical images, i.e. images where a disease is present and images where a disease is not present.

The augmentation mechanisms and resulting training of the convolutional neural network, machine learning model, or cognitive classification logic of the illustrative embodiments provide higher accuracy for classifying normal versus abnormal medical images (those having an abnormality present) when compared to known techniques. Moreover, the illustrative embodiments provide automated mechanisms for expanding or augmenting the initial small size dataset of annotated medical images, which significantly reduces the amount of time, resources, and human effort needed to produce a sufficient size training medical image dataset for training a classifier. Furthermore, the resulting trained classifier is more tolerant of data presented for classification from new domain sources as the trained classifier is trained to operate on unlabeled real image data.

The illustrative embodiments provide a framework by which to build a discriminator that separates images depicting abnormalities, e.g., disease instances, from normal medical images, e.g., normal chest X-ray images. In order to build such a discriminator, the framework of the illustrative embodiments utilize a GAN in semi-supervised training. The semi-supervised GAN-based framework, or architecture, involves an adaptation of a GAN generator G to take advantage of both labeled and unlabeled data. As the GAN-based framework converges, the discriminator D separates generated medical images from real medical images, as well as real medical images representing abnormalities from real medical images representing normal medical images, i.e. those that do not have an abnormality (e.g., disease) present in the medical image. As a result, both labeled and unlabeled data can contribute to the convergence of the model. This is useful for scenarios where there is a small amount of labeled (annotated) medical image data, or no labeled medical image data, and a large amount of unlabeled (non-annotated) medical image data.

The training of the generator of the GAN to generate fake or synthetic medical images that approximate real medical images to a level that the discriminator of the GAN is fooled by the generated medical images, permits the generator to be used as an additional source of unlabeled medical images that may be used to expand a training medical image data set that can be used to train a discriminator that is configured, by the mechanisms of the illustrative embodiments, to evaluate labeled, unlabeled, and generated (fake) medical image data. The training of the discriminator is performed such that the discriminator is able to determine the features of medical images indicative of real normal, real abnormal, fake normal, and fake abnormal medical images and provide high accuracy in the classification of input medical images into these classes. The training of the discriminator to operate on unlabeled medical image data makes the discriminator robust to re-training or adaptation based on new sources of medical imaging data.

Thus, when the GAN is employed with a new data source, such as a new client of the GAN based classifier service, the GAN may be adapted or re-trained for use with the new data source in a manner that does not require time consuming and resource intensive processes for labeling medical imaging data. That is, because the GAN is trained to obtain high accuracy with a relatively small set of labeled medical imaging data, in one methodology the adaptation or re-training of the GAN for the new data source may involve training the GAN on a small set of known labeled medical image data itself, such as from a known trusted source, e.g., a known trusted third party source of medical image data such as National Institute of Health (NIH) medical image data sources, for example. In such an embodiment, the medical image data obtained from known trusted source may be medical image data comprising medical images from a similar medical domain as the medical images that are provided in the new data source, e.g., if the new data source provides medical images for cardiovascular disease evaluations, then the medical images obtained from the known trusted source may similarly be labeled medical images in the cardiovascular disease domain.

Alternatively, the methodology for adapting or re-training the GAN may comprise training the GAN using a small set of known labeled medical image data as well as a relatively larger set of unlabeled medical image data from the new data source. This may require some efforts on the part of subject matter experts (SMEs) to label a small subset of the new data source's data to allow for re-training or adapting of the GAN, but this small set of medical image data that is labeled is significantly smaller than the full set of medical image data in the new data source and thus, is a minimized set of medical image data requiring a significantly reduced amount of effort and resources than would otherwise be required should the entire medical image data of the new data source be required to be labeled. That is, as the GAN is configured to perform training on both labeled and unlabeled medical image data, the new data source's unlabeled medical image data may be used in the re-training without needing the owners or operators of the new data source to label their medical image data.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the illustrative embodiments of the present invention provides a methodology, apparatus, system and computer program product for performing medical image dataset augmentation, or expansion, using a generative adversarial network framework or architecture. The illustrative embodiments adapt a GAN mechanism to operate on real labeled medical image data, real unlabeled medical image data, and generated medical image data generated by a generator G of the GAN mechanism. The generator G receives random noise and generates a fake image. The discriminator D is adapted to receive real labeled image data, real unlabeled image data, and generated image data and operates on the data to identify whether the input medical image data is a medical image representing a real normal image, a real abnormal image, or a fake (generated) image. The GAN is trained using the real labeled image data, real unlabeled image data, and generated image data such that as the model converges, the discriminator D separates generated from real medical images, and further separates real disease medical images, or abnormal medical images in which an abnormality is present, from real normal medical images. As a result, both labeled and unlabeled data can contribute to the convergence of the model.

Once the GAN is trained in this manner, the generator G may be applied to generate fake (generated) images to augment, or even replace, a training set of images, for training of a classifier, such as a convolutional neural network (CNN) or other machine learning model. For example, a CNN disease classifier, such as the discriminator D of the GAN or another external CNN disease classifier, may be trained using generated (fake) medical images and actual images. As the fake images greatly approximate true images, they provide an augmentation to the actual (real) medical images in the training image dataset, with the expanded training image dataset providing greater accuracy in the training of the CNN disease classifier. Once the CNN disease classifier is trained using the augmented set of training medical images, the CNN disease classifier may be used with new medical images to classify the medical images as indicating disease or abnormality presence or normality.

Figure 2A:
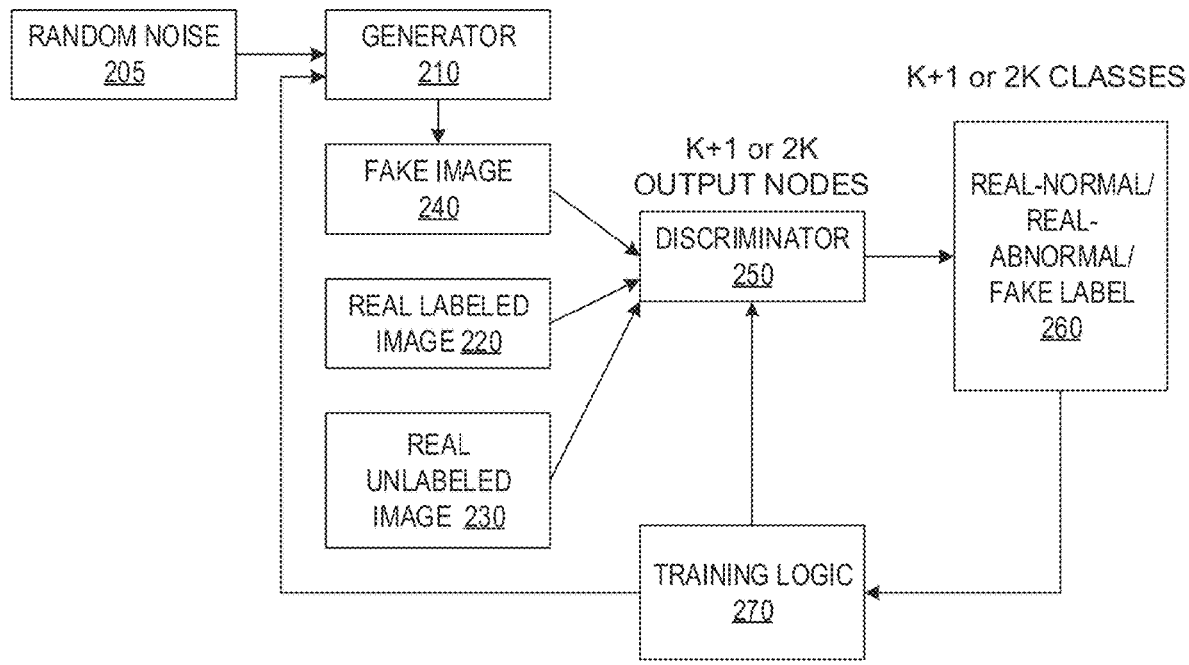

FIGS. 2A and 2B are example diagrams illustrating a semi-supervised GAN-based framework or architecture in accordance with one illustrative embodiment. FIG. 2A is an example block diagram illustrating the semi-supervised GAN-based framework, while FIG. 2B is a more graphical representation of the semi-supervised GAN-based framework, in accordance with one illustrative embodiment. As shown in FIGS. 2A and 2B, the GAN comprises a generator G 210 that receives a noise vector z, which may be sampled random Gaussian noise or condition with structured input. The generator G 210 is a convolutional neural network that transforms the noise vector z 205 input into an unlabeled image. The discriminator D 250 is a convolutional neural network that attempts to discriminate the input image data into one of a plurality of classes, e.g., real image normal, real image abnormal, or generated (fake) image. In one example embodiment, the discriminator D 250 outputs a vector 260 having values indicating whether the discriminator D 250 has determined the input image data to be associated with a real image normal, real image abnormal, or fake image.

In some implementations, such as that shown in FIGS. 2A and 2B, the discriminator D 250 comprises K+1 output nodes for outputting values of the vector 260 indicative of which of K+1 classes the discriminator D 250 has determined the input medical image data to be associated with. That is, there may be K classes in which one of the K classes is a normal medical image, i.e. a medical image in which no abnormality is identified. Other classes of the K classes may represent different types of abnormalities for which the discriminator D 250 is trained to identify. The K+1 class is a class for generated or fake medical image data. For example, the discriminator D 250 may classify medical images as either real-normal, real-abnormal (e.g., cardiovascular disease present), or fake and the corresponding labels in the output vector 260 may be set to values indicative of the classification, e.g., 0 or 1 associated with corresponding vector slots associated with the different classes.

In other illustrative embodiments, the discriminator D 250 may have 2K output nodes corresponding to 2K classes and the output vector 260 may have corresponding 2K vector slots corresponding to the 2K labels. In this embodiment, there are separate output nodes for combinations of real/fake normal and abnormal classes. For example, there may be separate classes for real-normal, real-abnormal, fake-normal, and fake-abnormal, where in this case K is 2, i.e. normal and abnormal, but K may be any number of classes depending on the desired implementation.

Thus, the unlabeled image generated by the generator G 210 is an attempt by the generator G 210 to fool the discriminator D 250 into generating an output indicating that the generated, or fake, image is in fact a real image. Of particular note, the generated images 240 output by the generator G 210 are fed into the discriminator D 250 along with real labeled image data 220 and real unlabeled image data 230. The discriminator D 250 is modified, such as with regard to the loss function employed by the neural network of the discriminator D 250 and the number of output nodes in the discriminator D 250 configuration, to receive these three types of input image data and determine a classification of the input image data into one of a plurality of classifications, as noted above. The loss function takes into account not only real labeled image data and generated (fake) image data, but also the real unlabeled image data. Through a training process, the loss function of the discriminator D 250 is minimized such that the GAN 200 converges and the generator G and discriminator D are trained, using the min-max gaming technique of the GAN 200, to an optimal state.

For the discriminator D 250 to be properly trained, the discriminator D 250 is trained via a semi-supervised training process to learn the features that are indicative of a normal medical image, an abnormal medical image, and a generated or fake medical image. For a real unlabeled medical image input to the discriminator D 250, the discriminator D is trained to properly identify the image as either fake or real, i.e. being one of a real normal image or a real abnormal image, even though the discriminator D 250 may get the actual label of normal or abnormal incorrect. For a real labeled medical image input, the discriminator D 250 is trained such that the discriminator D 250 is able to differentiate the image as fake or being one of a real normal image or a real abnormal image, and to determine correctly whether it is a real normal image or a real abnormal image. For generated (fake) images generated by the generator 210 as input to the discriminator D 250, the discriminator D 250 is trained to properly identify the image as being a generated or fake medical image.

In one illustrative embodiment of the present invention, the generator G 210 is configured to receive a 100×1 input vector z 205 which is projected and rescaled. The generator G 210 then processes the input vector z 205 via four convolutional layers with 2D-upsampling layers interlaced in-between to scale to an appropriate image size, e.g., 128×128 image size. To avoid sparse gradients, most nonlinear activations are applied with a leaky rectified linear unit (ReLU) function which has a small negative slope for the negative domain. The discriminator D 250 is a similar network to the generator G 210 with a series of convolutions with stride of 2 to replace the need for max-pooling. Dropout is used for regularization and leaky ReLU is again used except for the final one node activation with a sigmoid function. A set of normal images may be used to trained the GAN 200 to produce samples of normal images. A second GAN may be trained using only abnormal training data to produce abnormal image samples. Each GAN may be trained for many epochs, e.g., 500 epochs, where an epoch is a measure of the number of times all of the training vectors are used once to update the weights of the neural network nodes.

For example, the example embodiment shown in FIGS. 2A and 2B may be primarily descriptive of a K+1 class implementation where only one generator is utilized. In other illustrative embodiments, there may be multiple different generators, resulting in multiples of K classes. For example, in the 2K class embodiment mentioned above, there may be 2 GANs, or generators of a GAN, for use in a binary classification, e.g., actual versus fake medical image. In the 2K classification implementation, one generator may generate fake medical images that include abnormalities and the other generator may generate fake medical images that do not include abnormalities. Thus, the generators are each trained to generate fake images that approximate real images, with regard to abnormal real images or normal real images, respectively.

It should be appreciated that the selection of the number of convolutional layers of the neural networks, image size, use of leaky ReLU, and other configuration elements discussed above may vary based on the desired implementation of the present invention and the illustrative embodiments of the present invention are not limited to those configuration elements mentioned above. This is just one illustrative embodiment provided for illustrative purposes.

The GAN architecture 200 shown in FIGS. 2A and 2B may be trained using a semi-supervised training technique. The main difference between a semi-supervised GAN implementation and an unsupervised GAN is the structure of the loss function of the neural network of the discriminator D 250 to incorporate both labeled and unlabeled real image data. The loss function can be divided into three parts. The output layer of the discriminator D 250, in one illustrative embodiment, has K+1 classes, where K=2 for normal and abnormal, and the K+1 class is for generated (fake) images. The loss function L is defined for each type of data (Llabeled, Lunlabeled, Lgenerated) separately and the total loss is used in optimization of the GAN 200:

$$L = Ll_{abeled} + L_{unlabeled} + L_{generated} \quad (3)$$

$$L_{labeled} = -E_{x,y\sim pdata} \log p_{model}(y|x, y < K+1) \quad (4)$$

$$L_{unlabeled} = -E_{x\sim pdata} \log(1 - p_{model}(y=K+1|x)) \quad (5)$$

$$L_{generated} = -E_{x\sim G} \log p_{model}(y=K+1|x) \quad (6)$$

where x corresponds to an image, y corresponds to the label, pdata is the real data distribution, G is the generator, and pmodel(.|.) is the predicted class probability. Thus, the loss function L takes into account an error for each type of image fed-forward through the discriminator D 250, and is used to update the weights of the nodes of the discriminator D 250 through a stochastic gradient descent based training, or other training methodology implemented by training logic 270.

As the loss function for unlabeled data shows, these samples can be classified as any of the K classes of interest (K=2 here) and contribute to loss when they are classified as generated class K+1. Similar loss functions may be provided for implementations in which there are 2K classes with separate error components for the various classes in such an implementation. As a result, this GAN architecture 200 allows the unlabeled real data to contribute to learning, reducing the amount of labeling effort required to achieve a desired level of accuracy.

For one illustrative implementation of the GAN 200 in FIGS. 2A and 2B is configured and implemented to identify cardiac abnormalities in chest X-rays. It should be appreciated, however, that the GAN 200 may be utilized with any image data sets, whether medical or otherwise. Moreover, with regard to medical images, the GAN 200 may be utilized with any anatomical portions of a biological entity, and any imaging technologies or modalities, without departing from the spirit and scope of the present invention.

To demonstrate the improvements made by the illustrative embodiment, in one illustrative embodiment in which the GAN 200 is employed to identify cardiac abnormalities in chest X-ray images, an example implementation was generated by the present inventors, two datasets of chest X-ray images were used. For example, one dataset was the National Institute of Health (NIH) prostate, lung, colorectal, and ovarian (PLCO) cancer dataset, while the other dataset was from the NIH Chest X-ray collection from Indiana University. In the NIH PLCO dataset (Dataset 1) there were approximately 196,000 X-ray digital images of which a subset of approximately 36,000 frontal chest X-rays were chosen. A subset of 4500 images were used with labels of normal or abnormal which were subsequently rescaled to 128×128 pixels and histogram equalized. FIG. 3 is an example diagram illustrating sample chest X-ray images from the NIH PLCO dataset with the left column corresponding to normal chest X-rays and the right column corresponding to abnormal chest X-rays due to cardiovascular abnormality. The abnormal class samples were originally tagged for any patient with cardiomegaly, congestive heart failure, or cardiac abnormality. A subsample of 100 images were taken to confirm correct ground-truthing with a trained radiologist. The second dataset (Dataset 2) from Indiana University, was used to examine performance of deep learned classifiers on different data source domains. 400 cases of normal chest X-rays were used and 313 cases of cardiomegaly (as the abnormal class) were used. The datasets were split into three groups, i.e. training, validation, and testing, in an 80:10:10 ratio.

The GAN 200 was trained on Dataset 1 and then tested using Dataset 2. Thereafter, the GAN 200 was trained on both datasets by treating Dataset 1 as labeled image data 220 and Dataset 2 as unlabeled image data 230. After training, the GAN 200 was tested on Dataset 2.

The results of the above implementation of the GAN 200 and the training and testing of the GAN 200, demonstrate the ability of the illustrative embodiments of the present invention to produce generated medical images that resemble chest X-rays from a qualitative perspective. Afterwards, vectors from the normal distribution (noise input to the generator) were randomly sampled to be fed forward through the generator G 210 network. As shown in FIG. 4, the sampled generated (fake) images capture the global structural elements such as the lungs, spine, heart, and visual signatures such as the ribs, aortic arch, and the unique curvature of the lower lungs.

Figures 5A, 5B:
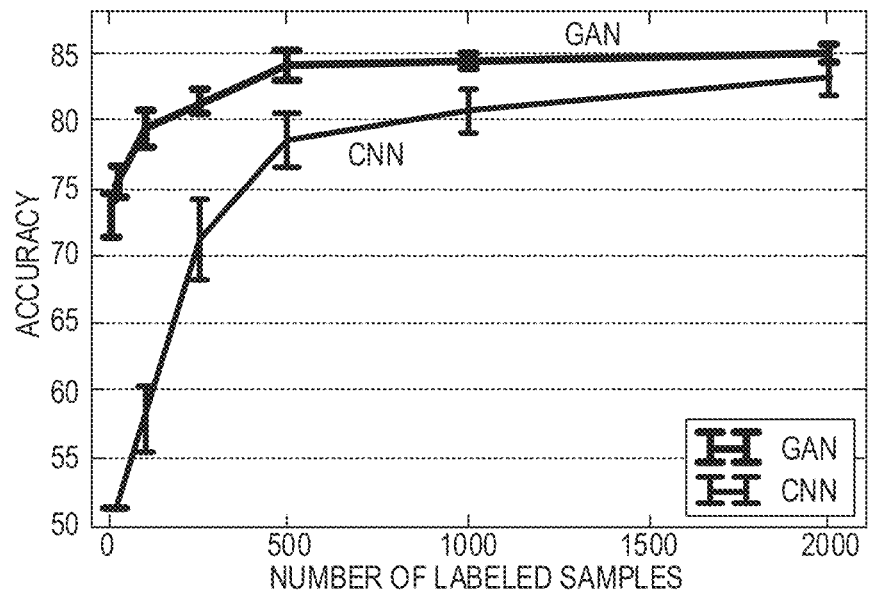
FIG. 5A is an example plot of accuracy performance of the semi-supervised GAN architecture of the illustrative embodiments compared to a conventional supervised convolutional neural network (CNN)
FIG. 5B is a table demonstrating a reduced numbered of labeled medical images required to achieve a comparable accuracy between the semi-supervised GAN of the illustrative embodiments and a conventional supervised CNN.

The results of the above implementation of the GAN 200 further demonstrate improved performance for image classification tasks when labeled data is scarce. As shown in FIGS. 5A and 5B, it can be seen that the GAN 200 requires an order of magnitude fewer labeled samples to achieve comparable results to a convolutional neural network (CNN) trained on Dataset 1. For example, the semi-supervised GAN 200 model of the illustrative embodiments needed only 10 labeled medical images for each class to achieve an accuracy of 73.08% while the conventional CNN required somewhere between 250 to 500 labeled medical images to achieve a similar accuracy.

The results of the above implementation of the GAN 200 further illustrate an improved performance of the classifier, e.g., discriminator D 250. Assuming each dataset has its associated biases from data collection, usually there is a drop in performance when the GAN is tested on a new dataset. When trained on 80% of Dataset 1, a conventional CNN is able to achieve 81.93% accuracy on a held-out 10% test set from Dataset 1. However, when the same conventional CNN is tested on all of Dataset 2, the accuracy drops to 57.8%, which is a hallmark over overfitting, as shown in the table of FIG. 6.

Figures 6, 8:
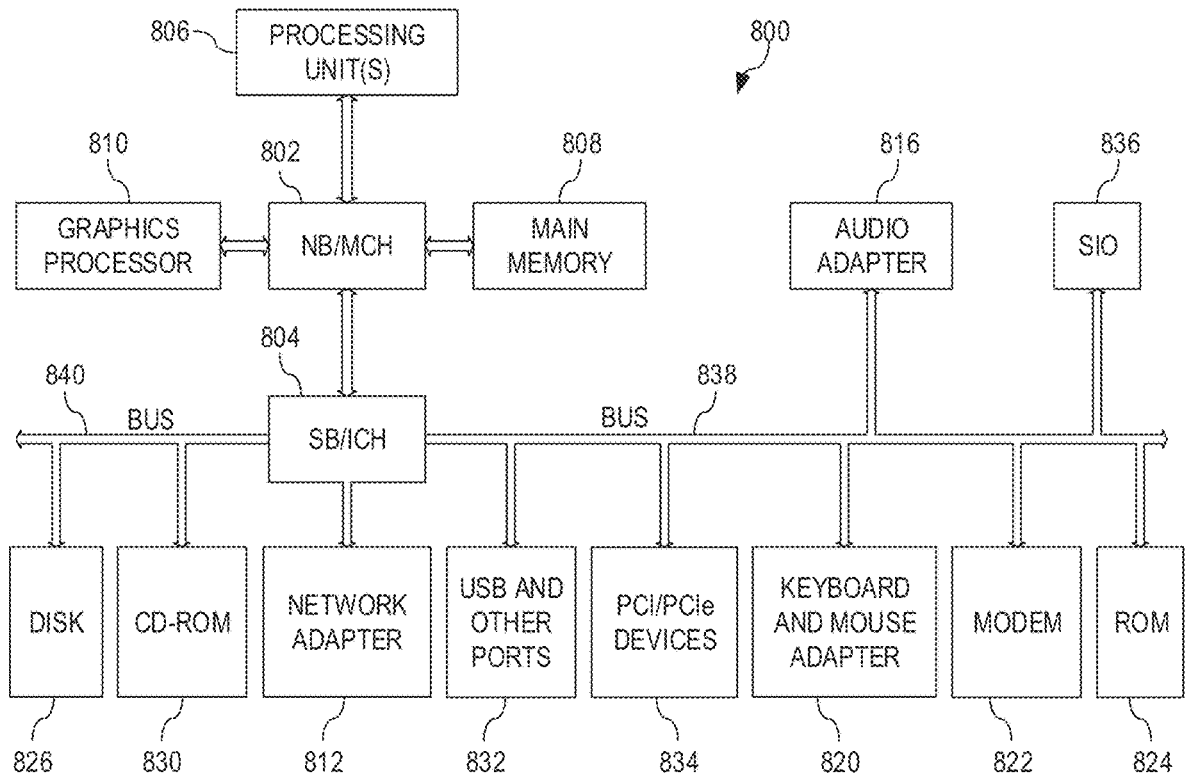
FIG. 6 is a table demonstrating robustness of the semi-supervised GAN of the illustrative embodiments to overfitting to domain source artifacts when compared to a conventional supervised CNN.
FIG. 8 is an example block diagram of a data processing system in which aspects of the illustrative embodiments may be implemented.

The semi-supervised GAN of the illustrative embodiments, under the same training scenario is more robust as it only drops to 76.4% in accuracy on Dataset 2, as shown in FIG. 6. Furthermore, when the semi-supervised GAN of the illustrative embodiments is trained on 100% of Dataset 1 with labels and 80% of Dataset 2 without labels, an accuracy of 93.7% was able to be achieved when tested on a 20% held-out from Dataset 2. Thus, without any labeling of Dataset 2, the classifier (e.g., discriminator D 250) of the GAN 200 is able to achieve high accuracy. Thus, the illustrative embodiments provide a low cost solution for model adaptation for a new data source as the GAN mechanisms of the illustrative embodiments remove the need for costly labeling of the data from the new data source prior to re-training.

Thus, the deep generative adversarial network (GAN) of the illustrative embodiments is able to learn the visual structure in medical imaging domains, such as in the chest X-ray medical imaging domain and others. Generated samples from the generator G network of the GAN present both the global and local structure that define particular classes of medical images. The semi-supervised GAN architecture of the illustrative embodiments is capable of learning from both labeled and unlabeled medical image data. As a result, the annotation effort is reduced considerably while being able to achieve similar performance through supervised training techniques. This may be attributed to the ability of the GAN architecture of the illustrative embodiments being able to learn structure in the unlabeled medical imaging data in a supervised learning fashion which significantly offsets the low number of labeled medical image data samples. In addition, the semi-supervised GAN architecture of the illustrative embodiments is robust to data source domain issues as demonstrated by the relatively smaller drop in accuracy of the semi-supervised GAN architecture relative to conventional supervised CNN approaches. Thus, if re-training the semi-supervised GAN architecture in a new domain is feasible, one can use unlabeled medical imaging data from the new domain rather than having to endure the costly process of labeling medical imaging data as would be needed in the conventional supervised CNN approaches.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

Figure 7:
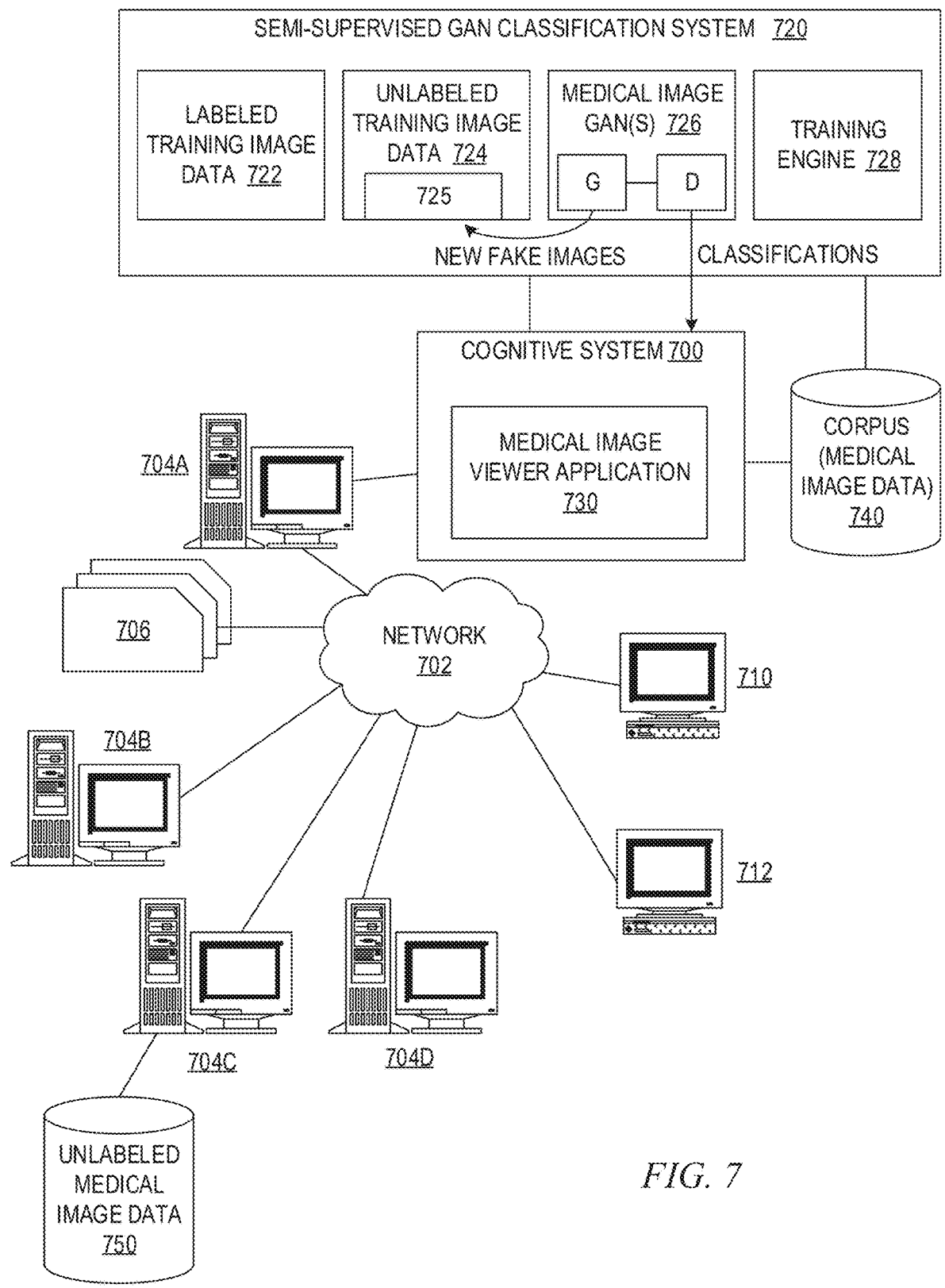
FIG. 7 is an example block diagram illustrative an implementation of the semi-supervised GAN of the illustrative embodiments of with a cognitive system providing a medical image viewer in accordance with one illustrative embodiment.

FIGS. 7-8 are directed to describing an example cognitive system for healthcare applications which implements a medical image viewer application 730 for viewing medical images and obtaining information about the medical images of particular patients. The cognitive system may also provide other cognitive functionality including treatment recommendations, patient electronic medical record (EMR) analysis and correlation with medical imaging data, and various other types of decision support functionality involving cognitive analysis and application of computer based artificial intelligence or cognitive logic to large volumes of data regarding patients. In some illustrative embodiments, the cognitive system may implement a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, medical image analysis logic, and the like, for example, as well as machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, medical image analysis logic, and other types of logic that emulate human thought processes using specially configured computing mechanisms. IBM Watson™ is an example of one such cognitive system with which the mechanisms of the illustrative embodiments may be utilized or in which the mechanisms of the illustrative embodiments may be implemented.

FIG. 7 depicts a schematic diagram of one illustrative embodiment of a cognitive system 700 implementing a medical image viewer application 730 in a computer network 702. The cognitive system 700 is implemented on one or more computing devices 704A-D (comprising one or more processors and one or more memories, and potentially any other computing device elements generally known in the art including buses, storage devices, communication interfaces, and the like) connected to the computer network 702. For purposes of illustration only, FIG. 7 depicts the cognitive system 700 being implemented on computing device 704A only, but as noted above the cognitive system 700 may be distributed across multiple computing devices, such as a plurality of computing devices 704A-D. The network 702 includes multiple computing devices 704A-D, which may operate as server computing devices, and 710-712 which may operate as client computing devices, in communication with each other and with other devices or components via one or more wired and/or wireless data communication links, where each communication link comprises one or more of wires, routers, switches, transmitters, receivers, or the like.

In some illustrative embodiments, the cognitive system 700 and network 702 enables question processing and answer generation (QA) functionality for one or more cognitive system users via their respective computing devices 710-712. In other embodiments, the cognitive system 700 and network 702 may provide other types of cognitive operations including, but not limited to, request processing and cognitive response generation which may take many different forms depending upon the desired implementation, e.g., cognitive information retrieval, training/instruction of users, cognitive evaluation of data, such as medical imaging data, or the like. Other embodiments of the cognitive system 700 may be used with components, systems, sub-systems, and/or devices other than those that are depicted herein.

In some illustrative embodiments, the client computing devices 710 and 712 may be used as a mechanism for logging onto or otherwise accessing the cognitive system 700 for purposes of viewing medical imaging studies for patients and perform operations for classifying and/or corroborating automated classification of such medical imaging studies. For example, a radiologist or other medical imaging subject matter expert (SME) may utilize a client computing device 710 to access the services and functionality provided by the cognitive system 700 and the medical image viewer application 730 to view medical images of one or more medical imaging studies stored in the corpus 740 for one or more patients. The user of the client computing device 710 may view the medical images and perform operations for annotating the medical images, adding notes to patient electronic medical records (EMRs), corroborate automatically identified classifications of the medical images and/or override incorrect classifications, and any of a plethora of other operations that may be performed through human-computer interaction based on the human's viewing of the medical images via the cognitive system 700.

As noted above, in some illustrative embodiments, the cognitive system 700 may be configured to implement a request processing pipeline that receive inputs from various sources. The requests may be posed in the form of a natural language question, natural language request for information, natural language request for the performance of a cognitive operation, or the like. For example, the cognitive system 700 receives input from the network 702, a corpus or corpora of electronic documents 706, cognitive system users, and/or other data and other possible sources of input. In one embodiment, some or all of the inputs to the cognitive system 700 are routed through the network 702. The various computing devices 704A-D on the network 702 include access points for content creators and cognitive system users. Some of the computing devices 704A-D include devices for a database storing the corpus or corpora of data 706 (which is shown as a separate entity in FIG. 1 for illustrative purposes only). Portions of the corpus or corpora of data 706 may also be provided on one or more other network attached storage devices, in one or more databases, or other computing devices not explicitly shown in FIG. 7. The network 702 includes local network connections and remote connections in various embodiments, such that the cognitive system 700 may operate in environments of any size, including local and global, e.g., the Internet.

The request processing pipeline of the cognitive system 700 may comprises a plurality of stages for processing an input question/request based on information obtained from the corpus or corpora of data 706 and/or 740. The pipeline generates answers/responses for the input question or request based on the processing of the input question/request and the corpus or corpora of data 706, 740. In some illustrative embodiments, the cognitive system 700 may be the IBM Watson™ cognitive system available from International Business Machines Corporation of Armonk, N.Y., which is augmented with the mechanisms of the illustrative embodiments described herein. More information about the pipeline of the IBM Watson™ cognitive system may be obtained, for example, from the IBM Corporation website, IBM Redbooks, as well as in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 7, the cognitive system 700 may operate in conjunction with a semi-supervised GAN classification system 720, in accordance with the mechanisms of the illustrative embodiments. The semi-supervised GAN classification system 720 may be implemented in specialized hardware, software executed on hardware, or any combination of specialized hardware and software executed on hardware. The semi-supervised GAN classification system 720 comprises one or more medical image GANs 726 specifically configured and trained in the manner previous described above with regard to one or more of the illustrative embodiments.

That is, the semi-supervised GAN classification system 720 comprises the medical image GAN(s) 726 which are trained using the labeled training image data 722 and unlabeled training image data 724 via the training engine logic 728. The labeled training image data 722, as discussed above, comprises a relatively small set of medical image data that is labeled by subject matter experts (SMEs), whereas the unlabeled training image data 724 is relatively larger and does not have such labels. Both the labeled and unlabeled training data 722, 724, as well as generated (fake) images generated by a generator G of the GAN 726 are used to train the GAN to produce additional generated (fake) medical images 725 approximating real medical images which can be used to augment the unlabeled training image data set 724, e.g., fake images 725 similar to that shown in FIG. 4. In addition, the discriminator D of the GAN 726 is trained to differentiate input medical image data into K+1 or 2K classes of medical images, depending on the implementation, using labeled and unlabeled training data as discussed above. The discriminator D of the medical imaging GAN(s) 726 may then be used as a classifier to classify medical image data from various medical imaging studies of patients as may be provided in the corpus 740, for example, and provide the classification information to the cognitive system 700 for performance of cognitive operations and/or viewing by a user via the medical image viewer application 730. The training engine 728 comprises the logic for determining how to modify weights of nodes in the neural networks of the generator G and discriminator D so as to converge the GANs 726 to an optimal state.

In one illustrative embodiment, the discriminator D of the GAN 726, once trained may be utilized as a classifier for classifying medical images into one of a plurality of classes. The classes comprise a class for normal medical images, i.e. medical images where no abnormality is identified, and one or more other classes indicative of one or more abnormalities or diseases. The number of abnormalities for which a GAN 726 is trained is implementation dependent. In some implementations separate GANs 726 may be trained and utilized for different types of abnormalities or diseases. Thus, a medical image, i.e. the data representing the medical image, may be submitted to a plurality of different GANs 726 which have been separately trained using the mechanisms of the illustrative embodiments, for different abnormality or disease classification and may operate on the medical image data in parallel to determine classifications of the medical image with regard to the different abnormalities or diseases. It can be appreciated that for one GAN 726, the outcome may be that the medical image is a normal medical image (because that GAN is not trained to identify an abnormality of the type actually present in the medical image data), whereas for a different GAN 726 the output may indicate an abnormality (because that GAN is trained to identify the abnormality of the type present in the medical image data). Thus, an aggregation of the outputs of the GANs 726 may be generated by the semi-supervised GAN classification system 720 and provided to the cognitive system 700 for use in cognitive operations and/or viewing by a user via the medical image viewer application 730.

As previously mentioned above, one benefit of the GAN based architecture of the illustrative embodiments is the robustness of the architecture with regard to handling new medical image data sources. Thus, for example, if a new client of the cognitive system 700 service, such as a new radiology lab, a new CT scan facility, a new hospital, or the like, is registered with the cognitive system 700, rather than having to have the client label the medical image data that it wishes to utilize with the cognitive system 700 and the semi-supervised GAN classification system 720 for purposes of classifying the medical image data, the mechanisms of the illustrative embodiments allow the trained GAN 726 to be adapted or re-trained for the new data source, or a new instance of the trained GAN 726 may be adapted or re-trained for the new data source, without having to label the new data source's medical image data.

For example, assume that a server 704C is associated with a medical imaging laboratory that decides to utilize the services of the cognitive system 700 and medical image viewer application 730. The server 704C provides a new data source 750 having new unlabeled medical image data that has not been previously processed by the cognitive system 700 and semi-supervised GAN classification system 720. The semi-supervised GAN classification system 720 may adapt or re-train the GAN 726 for operation with the new data source 750. However, in some situations, it may not be possible to re-train the GAN 726 when presented with a new data source at a new client site, e.g., server 704C. In such a situation, if the GAN 726 has been trained, at the time of training with the new client's own data, there may be a smaller reduction in accuracy when the new client's data is utilized.

Even in the case where re-training of the GAN 726 for use with a new client, e.g., server 704C, is an option, typically one does not have the luxury of obtaining all of the new client data in a labelled format, and the client system 704C may only be able to provide their data as unlabeled data. In this scenario, methodologies may be utilized in which the new client's unlabeled data is used to train the GAN 726 using the semi-supervised architecture, which is specifically configured to permit the use of unlabelled data. These methodologies may, in cases where some labeled data is able to be provided, such as from a third party source or from a labeling of a small subset of the new client's data, may involve some re-training of the GAN 726 based on the small set of labeled data, but with a relatively larger set of unlabeled data.

For example, in some illustrative embodiments, a first methodology may comprise a semi-supervised GAN training architecture as describe above in which only a relatively small training dataset is utilized that includes only labeled medical image data. In one illustrative embodiment, a small number of the medical images present in the unlabeled medical image data 750 of the new client need to be labeled and provided as training input into the semi-supervised GAN classification system 720 to re-train the medical image GAN 726. As shown in FIG. 5B above, a small labeled training medical image data set may be used to obtain a relatively high level of accuracy in the training of the medical image GAN 726. As shown in FIG. 6, while a small reduction in accuracy may be obtained from training only on a small labeled training medical image data set, the accuracy is still comparable to the accuracy of conventional supervised CNNs trained on relatively large labeled medical image datasets.

In one illustrative embodiment, a second methodology may comprise a semi-supervised GAN 726 that is re-trained using both a small set of labeled medical image data from a known and trusted source of labeled medical image data, such as NIH, for example, and a relatively larger set of unlabeled medical image data. In this methodology, the new and unlabeled medical image data, or a portion thereof, from the new data source 750 may be utilized as the set of unlabeled medical image data for re-training the semi-supervised GAN 726. In either the first or second methodology, extensive labeling of the unlabeled medical image data in the new data source 750 is not required in order for the semi-supervised GAN classification system 720 to be trained for use with the new data source 750 due to the architecture provided by the mechanisms of the illustrative embodiments which permit training of the GAN 726 based on both labeled and unlabeled medical image data.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 8 is provided as an example of one type of data processing system in which aspects of the present invention may be implemented. Many other types of data processing systems may be likewise configured to specifically implement the mechanisms of the illustrative embodiments.

FIG. 8 is a block diagram of an example data processing system in which aspects of the illustrative embodiments are implemented. Data processing system 800 is an example of a computer, such as a server 704A-D or client 710-712 in FIG. 7, in which computer usable code or instructions implementing the processes for illustrative embodiments of the present invention are located. In one illustrative embodiment, FIG. 8 represents a server computing device, such as a server 704A, which, which implements a cognitive system 700 and medical image viewer application 730, where the server 704A further is specifically configured and executes hardware and/or software logic to implement the semi-supervised GAN classification system 720 of FIG. 7.

In the depicted example, data processing system 800 employs a hub architecture including North Bridge and Memory Controller Hub (NB/MCH) 802 and South Bridge and Input/Output (I/O) Controller Hub (SB/ICH) 804. Processing unit 806, main memory 808, and graphics processor 810 are connected to NB/MCH 802. Graphics processor 810 is connected to NB/MCH 802 through an accelerated graphics port (AGP).

In the depicted example, local area network (LAN) adapter 812 connects to SB/ICH 804. Audio adapter 816, keyboard and mouse adapter 820, modem 822, read only memory (ROM) 824, hard disk drive (HDD) 826, CD-ROM drive 830, universal serial bus (USB) ports and other communication ports 832, and PCI/PCIe devices 834 connect to SB/ICH 804 through bus 838 and bus 840. PCI/PCIe devices may include, for example, Ethernet adapters, add-in cards, and PC cards for notebook computers. PCI uses a card bus controller, while PCIe does not. ROM 824 may be, for example, a flash basic input/output system (BIOS).

HDD 826 and CD-ROM drive 830 connect to SB/ICH 804 through bus 840. HDD 826 and CD-ROM drive 830 may use, for example, an integrated drive electronics (IDE) or serial advanced technology attachment (SATA) interface. Super I/O (SIO) device 836 is connected to SB/ICH 804.

An operating system runs on processing unit 806. The operating system coordinates and provides control of various components within the data processing system 800 in FIG. 8. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 800.

As a server, data processing system 800 may be, for example, an IBM® eServer™ System p® computer system, running the Advanced Interactive Executive) (AIX®) operating system or the LINUX® operating system. Data processing system 800 may be a symmetric multiprocessor (SMP) system including a plurality of processors in processing unit 806. Alternatively, a single processor system may be employed.

Instructions for the operating system, the object-oriented programming system, and applications or programs are located on storage devices, such as HDD 826, and are loaded into main memory 808 for execution by processing unit 806. The processes for illustrative embodiments of the present invention are performed by processing unit 806 using computer usable program code, which is located in a memory such as, for example, main memory 808, ROM 824, or in one or more peripheral devices 826 and 830, for example.

A bus system, such as bus 838 or bus 840 as shown in FIG. 8, is comprised of one or more buses. Of course, the bus system may be implemented using any type of communication fabric or architecture that provides for a transfer of data between different components or devices attached to the fabric or architecture. A communication unit, such as modem 822 or network adapter 812 of FIG. 8, includes one or more devices used to transmit and receive data. A memory may be, for example, main memory 808, ROM 824, or a cache such as found in NB/MCH 802 in FIG. 8.

Those of ordinary skill in the art will appreciate that the hardware depicted in FIGS. 7 and 8 may vary depending on the implementation. Other internal hardware or peripheral devices, such as flash memory, equivalent non-volatile memory, or optical disk drives and the like, may be used in addition to or in place of the hardware depicted in FIGS. 7 and 8. Also, the processes of the illustrative embodiments may be applied to a multiprocessor data processing system, other than the SMP system mentioned previously, without departing from the spirit and scope of the present invention.

Moreover, the data processing system 800 may take the form of any of a number of different data processing systems including client computing devices, server computing devices, a tablet computer, laptop computer, telephone or other communication device, a personal digital assistant (PDA), or the like. In some illustrative examples, data processing system 800 may be a portable computing device that is configured with flash memory to provide non-volatile memory for storing operating system files and/or user-generated data, for example. Essentially, data processing system 800 may be any known or later developed data processing system without architectural limitation.

Figure 9:
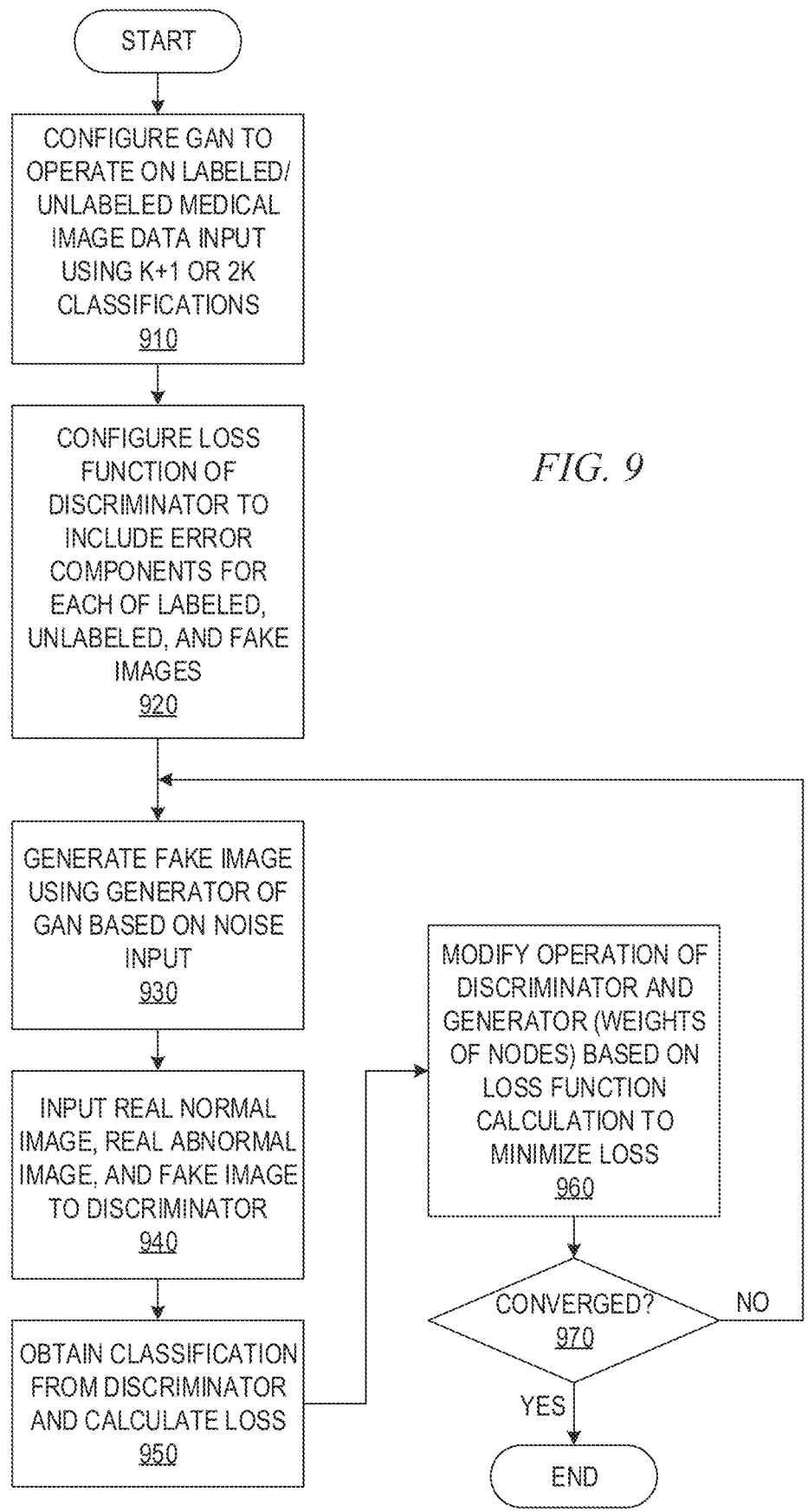
FIG. 9 is a flowchart outlining an example operation for training a semi-supervised GAN in accordance with one illustrative embodiment.

FIG. 9 is a flowchart outlining an example operation for training a semi-supervised GAN in accordance with one illustrative embodiment. As shown in FIG. 9, the operation starts by configuring the GAN to operate on labeled/unlabeled medical image data input using K+1 or 2K classifications (step 910). The GAN is further configured with a loss function of the discriminator to include error components for each of the labeled, unlabeled, and fake images (step 920). The generator of the GAN then generates a fake image based on an input noise vector z (step 930). In addition, real normal image data and real abnormal image data are provided to the discriminator of the GAN along with the generated (fake) image data (step 940). The discriminator provides a classification of the image data and a calculated loss based on the configured loss function (step 950). The operation of the GAN, e.g., the weights of nodes in the generator and discriminator, is then modified based on the loss function calculation and training logic that operates to minimize the loss function (step 960). A determination is made as to whether or not the GAN training has converged (step 970). If so, the operation terminates. Otherwise, the operation returns to step 930 with further training based on additional fake image generation.

Figure 10:
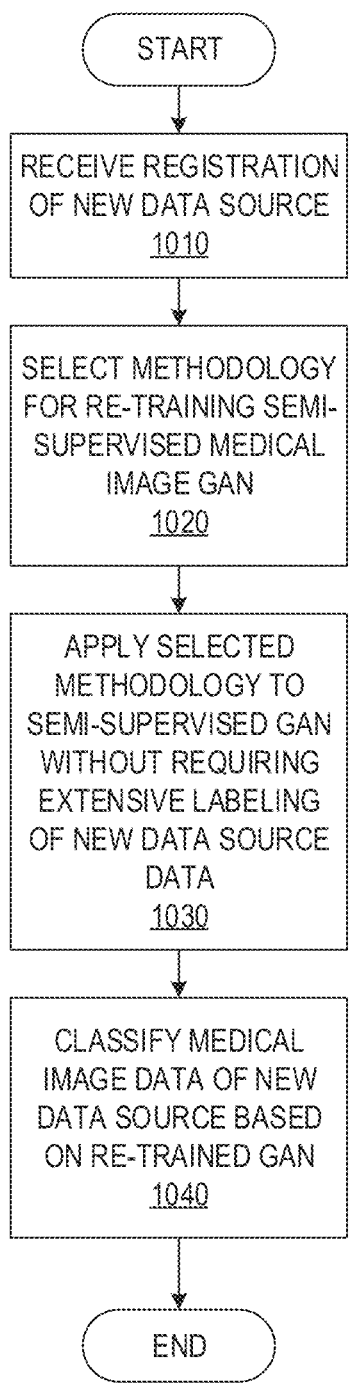
FIG. 10 is a flowchart outlining an operation for re-training a semi-supervised GAN for a new data source in accordance with one illustrative embodiment.

FIG. 10 is a flowchart outlining an operation for re-training a semi-supervised GAN for a new data source in accordance with one illustrative embodiment. As shown in FIG. 10, the operation comprises receiving the registration of a new data source (step 1010). A methodology for re-training the semi-supervised medical image GAN is selected for the new data source (step 1020). The selected methodology is then applied without requiring extensive labeling of the new data source data (step 1030). After training, the medical image data in the new data source is then classified using the re-trained GAN (step 1040) and the operation terminates.

It should be appreciated that while the above described illustrative embodiments are especially well suited for implementation with medical image data and classifying medical images, the illustrative embodiments are not limited to such. Rather, the mechanisms of the illustrative embodiments may be utilized with any implementation in which image data, whether medical or otherwise, is classified into one of a plurality of classes. The principles of the illustrative embodiments with regard to providing an architecture that can be trained using both labeled and unlabeled image data are equally applicable regardless of the particular type of image data being operated on. Moreover, the various cognitive operations that are supported by the classifications may vary depending on the type of image data operated on and the classifications employed. For example, facial recognition mechanisms, biometric security mechanisms, and the like, may all implement classifications of image data and may benefit from the implementation of a GAN based architecture such as that described herein. Thus, many modifications may be made to the mechanisms described above without departing from the spirit and scope of the present invention.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to configure the processor to implement a machine learning training model, the method comprising:

training, by the machine learning training model, an image generator of a generative adversarial network (GAN) to generate medical images approximating actual medical images;

augmenting, by the machine learning training model, a set of training medical images to include one or more generated medical images generated by the image generator of the GAN;

training, by the machine learning training model, a machine learning model based on the augmented set of training medical images to identify anomalies in medical images; and applying the trained machine learning model to new medical image inputs to classify the medical images as having an anomaly or not, wherein the machine learning model is a discriminator of the GAN which is configured to receive, as input, actual labeled medical image data, actual unlabeled medical image data, and generated medical image data generated by the image generator of the GAN, and wherein training the machine learning model comprises training the discriminator to generate an output comprising an output value for each of a plurality of classifications, and wherein the plurality of classifications comprises a first classification for real-normal image data indicating input image data to be actual image data representing a normal medical condition, at least one second classification for real-abnormal image data indicating input image data to be actual image data representing a corresponding abnormal medical condition, and a third classification for generated image data indicating input image data to be image data generated by the image generator.

2. The method of claim 1, wherein training a generator of the GAN to generate medical images approximating actual medical images, further comprises:

receiving, by the image generator of the GAN, at least one medical image showing an anatomical structure;

inputting, by a noise generator, a noise input to the image generator;

generating, by the image generator, at least one generated image based on a combination of the at least one medical image and the noise input;

providing the at least one medical image and the at least one generated image to the discriminator of the machine learning training image;

analyzing, by the discriminator, the at least one medical image and the at least one generated image to label the at least one medical image and the at least one generated image as either being an actual medical image or a generated medical image; and modifying an operational parameter of the generator based on the results of analyzing the at least one medical image and the at least one generated image by the discriminator.

3. The method of claim 1, wherein the GAN is trained to classify medical images with regard to whether or not the medical images contain an abnormality.

4. The method of claim 1, wherein the discriminator is trained, using an adversarial training technique based on the augmented set of training medical images, to discriminate between medical images showing anomalies and medical images showing normal medical conditions.

5. The method of claim 1, wherein training the image generator comprises training the image generator based on both labeled training medical images and non-labeled medical images, and wherein the training is based on a feedback obtained from the output of the discriminator.

6. The method of claim 1, wherein training, by the machine learning training model, the image generator to generate medical images approximating actual medical images comprises:
   training the discriminator of the GAN to separate generated medical images from actual medical images and actual medical images showing a normal medical condition from actual medical images showing an abnormal medical condition; and
   training the image generator to generate medical images that cause the discriminator to fail to correctly discriminate the generated medical images from actual medical images for a predetermined ratio of instances indicating convergence of the training of the GAN.

7. The method of claim 1, wherein the discriminator of the GAN is a convolutional neural network with K+1 output nodes, where K is a number of classes of abnormalities that the machine learning model is configured to identify in input medical images and the K+1 class is a class indicating an input medical image to be a generated medical image from the image generator, and wherein the discriminator outputs, for each input medical image, a corresponding vector output having K+1 values indicating into which class the discriminator classifies the input medical image.

8. The method of claim 1, wherein the discriminator is a convolutional neural network with 2K output nodes, where K is a number of classes of abnormalities that the machine learning model is configured to identify in input medical images and for each class in the K number of classes, there is a separate output node indicating whether the input medical image is a generated medical image from the image generator, or an actual medical image, and wherein the discriminator outputs, for each input medical image, a corresponding vector output having 2K values indicating into which class the discriminator classifies the input medical image.

9. The method of claim 1, further comprising:
   configuring a loss function of the discriminator of the GAN to include error components for each of actual labeled medical images, actual unlabeled medical images, and generated medical images, wherein training the image generator of the GAN to generate medical images approximating actual medical images comprises minimizing the loss function of the discriminator.

10. The method of claim 1, wherein the generator is one of a plurality of generators, and wherein at least one generator in the plurality of generators is trained to generate medical images approximating actual medical images having a normal medical condition depicted, and wherein at least one other generator in the plurality of generators is trained to generate medical images approximating actual medical images having an abnormal medical condition depicted.

11. A computer program product comprising a computer readable storage medium having a computer readable program stored therein, wherein the computer readable program, when executed on a data processing system, causes the data processing system to implement a machine learning training model that operates to:
   train an image generator of a generative adversarial network (GAN) to generate medical images approximating actual medical images;
   augment a set of training medical images to include one or more generated medical images generated by the image generator of the GAN;
   train a machine learning model based on the augmented set of training medical images to identify anomalies in medical images; and
   apply the trained machine learning model to new medical image inputs to classify the medical images as having an anomaly or not, wherein the machine learning model is a discriminator of the GAN which is configured to receive, as input, actual labeled medical image data, actual unlabeled medical image data, and generated medical image data generated by the image generator of the GAN, and wherein training the machine learning model comprises training the discriminator to generate an output comprising an output value for each of a plurality of classifications, and wherein the plurality of classifications comprises a first classification for real-normal image data indicating input image data to be actual image data representing a normal medical condition, at least one second classification for real-abnormal image data indicating input image data to be actual image data representing a corresponding abnormal medical condition, and a third classification for generated image data indicating input image data to be image data generated by the image generator.

12. The computer program product of claim 11, wherein the computer readable program further causes the machine learning training model to train the generator of the GAN to generate medical images approximating actual medical images, at least by:
   receiving, by the image generator of the GAN, at least one medical image showing an anatomical structure;
   inputting, by a noise generator, a noise input to the image generator;
   generating, by the image generator, at least one generated image based on a combination of the at least one medical image and the noise input;
   providing the at least one medical image and the at least one generated image to the discriminator of the machine learning training image;
   analyzing, by the discriminator, the at least one medical image and the at least one generated image to label the at least one medical image and the at least one generated image as either being an actual medical image or a generated medical image; and
   modifying an operational parameter of the generator based on the results of analyzing the at least one medical image and the at least one generated image by the discriminator.

13. The computer program product of claim 11, wherein the GAN is trained to classify medical images with regard to whether or not the medical images contain an abnormality.

14. The computer program product of claim 11, wherein the discriminator is trained, using an adversarial training technique based on the augmented set of training medical images, to discriminate between medical images showing anomalies and medical images showing normal medical conditions.

15. The computer program product of claim 11, wherein the computer readable program further causes the machine learning training model to train the image generator at least by training the image generator based on both labeled training medical images and non-labeled medical images, and wherein the training is based on a feedback obtained from the output of the discriminator.

16. The computer program product of claim 11, wherein the computer readable program further causes the machine learning training model to train the image generator to generate medical images approximating actual medical images at least by:

training the discriminator of the GAN to separate generated medical images from actual medical images and actual medical images showing a normal medical condition from actual medical images showing an abnormal medical condition; and training the image generator to generate medical images that cause the discriminator to fail to correctly discriminate the generated medical images from actual medical images for a predetermined ratio of instances indicating convergence of the training of the GAN.

17. The computer program product of claim 11, wherein the discriminator of the GAN is a convolutional neural network with K+1 output nodes, where K is a number of classes of abnormalities that the machine learning model is configured to identify in input medical images and the K+1 class is a class indicating an input medical image to be a generated medical image from the image generator, and wherein the discriminator outputs, for each input medical image, a corresponding vector output having K+1 values indicating into which class the discriminator classifies the input medical image.

18. The computer program product of claim 11, wherein the discriminator is a convolutional neural network with 2K output nodes, where K is a number of classes of abnormalities that the machine learning model is configured to identify in input medical images and for each class in the K number of classes, there is a separate output node indicating whether the input medical image is a generated medical image from the image generator, or an actual medical image, and wherein the discriminator outputs, for each input medical image, a corresponding vector output having 2K values indicating into which class the discriminator classifies the input medical image.

19. The computer program product of claim 11, wherein the computer readable program further causes the machine learning training model to:

configure a loss function of the discriminator of the GAN to include error components for each of actual labeled medical images, actual unlabeled medical images, and generated medical images, wherein training the image generator of the GAN to generate medical images approximating actual medical images comprises minimizing the loss function of the discriminator.

20. An apparatus comprising:

at least one processor; and at least one memory coupled to the at least one processor, wherein the at least one memory comprises instructions which, when executed by the at least one processor, cause the at least one processor to implement a machine learning training model that operates to:

train an image generator of a generative adversarial network (GAN) to generate medical images approximating actual medical images;

augment a set of training medical images to include one or more generated medical images generated by the image generator of the GAN;

train a machine learning model based on the augmented set of training medical images to identify anomalies in medical images; and apply the trained machine learning model to new medical image inputs to classify the medical images as having an anomaly or not, wherein the machine learning model is a discriminator of the GAN which is configured to receive, as input, actual labeled medical image data, actual unlabeled medical image data, and generated medical image data generated by the image generator of the GAN, and wherein training the machine learning model comprises training the discriminator to generate an output comprising an output value for each of a plurality of classifications, and wherein the plurality of classifications comprises a first classification for real-normal image data indicating input image data to be actual image data representing a normal medical condition, at least one second classification for real-abnormal image data indicating input image data to be actual image data representing a corresponding abnormal medical condition, and a third classification for generated image data indicating input image data to be image data generated by the image generator.

* * * * *